(12) United States Patent
Pompili et al.

(10) Patent No.: US 10,016,423 B2
(45) Date of Patent: Jul. 10, 2018

(54) SOLID FORMS OF NILOTINIB HYDROCHLORIDE

(71) Applicant: Apotex Inc., Toronto (CA)

(72) Inventors: Matthew Pompili, Toronto (CA); David A. Stradiotto, Brantford (CA); Probal Kanti Datta, Hamilton (CA)

(73) Assignee: Apotex Inc., Toronto, Ontario (CA)

( * ) Notice: Subject to any disclaimer, the term of this patent is extended or adjusted under 35 U.S.C. 154(b) by 0 days.

(21) Appl. No.: 15/518,895

(22) PCT Filed: Oct. 15, 2015

(86) PCT No.: PCT/CA2015/000534
§ 371 (c)(1),
(2) Date: Apr. 13, 2017

(87) PCT Pub. No.: WO2016/058081
PCT Pub. Date: Apr. 21, 2016

(65) Prior Publication Data
US 2017/0239247 A1 Aug. 24, 2017

Related U.S. Application Data

(60) Provisional application No. 62/064,625, filed on Oct. 16, 2014.

(51) Int. Cl.
| | |
|---|---|
| A61K 31/506 | (2006.01) |
| C07D 401/14 | (2006.01) |
| C07C 59/185 | (2006.01) |
| C07C 51/41 | (2006.01) |
| A61K 47/48 | (2006.01) |

(52) U.S. Cl.
CPC ...... *A61K 31/506* (2013.01); *A61K 47/48038* (2013.01); *C07C 51/412* (2013.01); *C07C 59/185* (2013.01); *C07D 401/14* (2013.01); *C07B 2200/13* (2013.01)

(58) Field of Classification Search
CPC .................................................. A61K 31/506
See application file for complete search history.

(56) References Cited

U.S. PATENT DOCUMENTS

| | | |
|---|---|---|
| 2013/0096304 A1 | 4/2013 | Sterimbaum et al. |
| 2013/0165465 A1 | 6/2013 | Manley et al. |
| 2013/0210847 A1* | 8/2013 | Kompella ............ C07D 401/14 514/275 |
| 2013/0245052 A1 | 9/2013 | Reddy et al. |
| 2015/0099885 A1 | 4/2015 | Piran et al. |
| 2015/0246901 A1 | 9/2015 | Chiodo et al. |
| 2015/0273070 A1 | 10/2015 | Li et al. |
| 2015/0274699 A1 | 10/2015 | Datta et al. |

FOREIGN PATENT DOCUMENTS

| | | | |
|---|---|---|---|
| WO | 2007015870 A2 | * | 2/2007 |
| WO | 2010054056 A2 | | 5/2010 |
| WO | 2010081443 A2 | | 7/2010 |
| WO | 2011033307 A1 | | 3/2011 |
| WO | 2011086541 A1 | | 7/2011 |
| WO | 2011163222 A1 | | 12/2011 |
| WO | 2012055351 A1 | | 5/2012 |
| WO | 2012070062 A2 | | 5/2012 |
| WO | 2012174082 A1 | | 12/2012 |
| WO | 2014059518 A1 | | 4/2014 |
| WO | 2014060449 A1 | | 4/2014 |

OTHER PUBLICATIONS

NLT HCl Crystalline Forms, IP.com: Prior Art Database, ip.com: IPCOM000187328D, 2009, 9(9B), pp. 1-7.
NLT HCl Crystalline Forms, IP.com: Prior Art Database, ip.com: IPCOM000190565D, 2009, 9(12B), pp. 1-5.
NLT HCl Crystalline Forms, IP.com: Prior Art Database, ip.com: IPCOM000183524D, 2009, pp. 1-12.
Crystalline Forms of NLT HCl, IP.com: Prior Art Database, 2010, ip.com: IPCOM000193749D, 10(3B), pp. 1-4.
Crystalline Form of 4 methyl-N-[3-(4-methyl-1H-imidazol-1-yl)-5-(trifluoromethyl)phenyl]-3-[[4-(3-pyridinyl)-2-pyrimidinyl]amino]benzamide, IP.com: Prior Art Database, 2010, ip.com: IPCOM000195326D, 10(5A), pp. 1-3.
Amorphous 4-methyl-N-[3-(4-methyl-1H-imidazol-1-yl)-5-(trifluoromethyl)phenyl]-3-[[4-(3-pyridinyl)-2-pyrimidinyl]amino]-benzamide salts, IP.com: Prior Art Database, 2010, ip.com: IPCOM000197295D, 10(7B), pp. 1-10.
Crystalline Form of 4-methyl-N-[3-(4-methyl-1H-imidazol-1-yl)-5-(trifluoromethyl)phenyl]-3-[[4-(3-pyridinyl)-2-pyrimidinyl]amino]benzamide salts, IP.com: Prior Art Database, 2010, ip.com: IPCOM000199113D, 10(9A), pp. 1-11.
Crystalline Form of 4-methyl-N-[3-(4-methyl-1H-imidazol-1-yl)-5-(trifluoromethyl)phenyl]-3-[[4-(3-pyridinyl)-2-pyrimidinyl]amino]-benzamide salts, IP.com: Prior Art Database, 2010, ip.com: IPCOM000201702D, 10(12A), pp. 1-9.
A crystallization process for 4-methyl-N-[3-(4-methyl-1H-imidazol-1-yl)-5-(trifluoromethyl)phenyl]-3-[[4-(3-pyridinyl)-2-pyrimidinyl]amino]-benzamide, IP.com: Prior Art Database, 2010, ip.com: IPCOM000202210D, 10(12B), pp. 1-3.

* cited by examiner

*Primary Examiner* — Alexander R Pagano
*Assistant Examiner* — Ebenezer Sackey
(74) *Attorney, Agent, or Firm* — The Webb Law Firm

(57) ABSTRACT

A solid form of Nilotinib hydrochloride, which exists as a co-crystal of nilotinib hydrochloride and levulinic acid having a molar ratio of nilotinib hydrochloride to levulinic acid of 1:2, and a process for the preparation of the co-crystal.

19 Claims, 4 Drawing Sheets

SOLID FORMS OF NILOTINIB HYDROCHLORIDE

CROSS-REFERENCE TO RELATED APPLICATIONS

This application is the United States national phase of International Application No. PCT/CA2015/000534 filed Oct. 15, 2015, and claims priority to U.S. Provisional Patent Application No. 62/064,625 filed Oct. 16, 2014, the disclosures of which are hereby incorporated in their entirety by reference.

TECHNICAL FIELD

The present invention is directed to Nilotinib hydrochloride and, in particular, to a solid form thereof.

BACKGROUND

Nilotinib hydrochloride (1) is a tyrosine kinase inhibitor used for the treatment of drug-resistant chronic myelogenous leukemia (CML). It is marketed in the United States as Tasigna™.

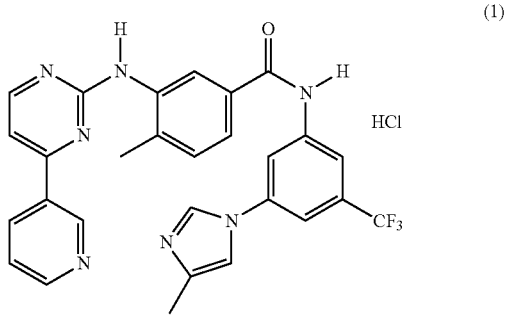 [SMILES: Cc1cn(-c2cc(NC(=O)c3ccc(C)c(Nc4nccc(-c5cccnc5)n4)c3)cc(C(F)(F)F)c2)cn1 ; Cl]

(1)

WO 2007/015870 A2 discloses crystalline forms of 4-methyl-N-[3-(4-methylimidazol-1-yl)-5-trifluoromethyl-phenyl)3-(4-pyridin-3-yl-pyrimidin-2-ylamino)-benzamide free base and salts thereof by various processes.

WO 2010/054056 A2 discloses crystalline forms of Nilotinib hydrochloride.

WO 2010/081443 A2 discloses co-crystals of inhibitors of tyrosine kinases, especially of Imatinib mesylate, which have been found as a suitable form of API for dosage forms, both conventional and with controlled release for medicaments of the second generation. Complexes of kinase inhibitors with functionalized polysaccharides form solid dispersions suitable for pharmaceutical applications.

WO 2011/086541 relates to a novel polymorph of 4-methyl-N-[3-(4-methyl-imidazol-1-yl)-5-(trifluoromethyl)-phenyl]-3-[(4-pyridin-3-yl-pyrimidin-2-yl)amino]benzamide(Nilotinib)monohydrochloride monohydrate, and to methods for preparing, pharmaceutical compositions comprising, and methods of treatment using said polymorph.

WO 2011/033307 A1 relates to nilotinib dihydrochloride and its hydrates, to methods for preparing nilotinib dihydrochloride and its hydrates, pharmaceutical compositions comprising nilotinib dihydrochloride and its hydrates, and methods of treatment using the same.

Crystalline Forms of NLT HCl are disclosed in *IP.com Journal* 2010, 10(3B), 11; *IP.com Journal* 2009, 9(12B), 14; *IP.com Journal* 2009, 9(9B), 61; and IP.com PriorArt DataBase.IP.com Number (May 26, 2009) IPCOM000183524D.

*IP.com Journal* 2010, 10(5A), 25 discloses a crystalline form of 4-methyl-N-[3-(4-methyl-1H-imidazol-1-yl)-5-(trifluoromethyl)phenyl]-3-[[4-(3-pyridinyl)-2-pyrimdinyl]amino]-benzamide.

*IP.com Journal* 2010, 10(12A), 18 and *IP.com Journal* 2010, 10(9A), 21 discloses crystalline forms of 4-methyl-N-[3-(4-methyl-1H-imidazol-1-yl)-5-(trifluoromethyl)phenyl]-3-[[4-(3-pyridinyl)-2-pyrimidinyl]amino]-benzamide salts.

*IP.com Journal* 2010, 10(12B), 28 discloses a crystallization process for 4-methyl-N-[3-(4-methyl-1H-imidazol-1-yl)-5-(trifluoromethyl)phenyl]-3-[[4-(3-pyridinyl)-2-pyrimidinyl]amino]-benzamide.

*IP.com Journal* 2010, 10(7B), 3 discloses amorphous 4-methyl-N-[3-(4-methyl-1H-imidazol-1-yl)-5-(trifluoromethyl)phenyl]-3-[[4-(3-pyridinyl)-2-pyrimidinyl]amino]-benzamide salts.

WO 2011/163222 A1 discloses that Nilotinib salts and crystalline forms thereof have been prepared and characterized.

WO 2012/055351 A1 discloses a crystal form of Nilotinib hydrochloride with X-ray powder diffraction as disclosed therein and a preparation method thereof.

WO 2012/070062 A2 discloses a novel crystalline form of Nilotinib hydrochloride, process for its preparation and pharmaceutical compositions comprising it.

WO 2012/174082 A1 discloses soluble pharmaceutical compositions of amorphous nilotinib or a pharmaceutically acceptable salt thereof using one or more organic acids that function as a solubilizing agent, increasing the bioavailability of nilotinib and suppressing the food effect associated with certain compositions of nilotinib. The pharmaceutical compositions are in the form of solid oral dosage forms, including capsules and tablets.

US 2013/0210847 A1 provides a process for the preparation of Nilotinib.

WO 2014/059518 A1 discloses solid forms of Nilotinib hydrochloride and methods of preparation of various crystalline solvates of Nilotinib HCl including benzyl alcohol, acetic acid, propylene glycol, and isopropanol. Nilotinib HCl is a tyrosine kinase inhibitor used for the treatment of drug resistant chronic myelogenous leukemia (CML).

WO 2014/060449 A1 relates to crystalline materials comprising nilotinib and a carboxylic acid, carboxylic acid ester, carboxylic acid amide or sulfonic acid as a co-crystal former, and to pharmaceutical compositions comprising said materials. The invention also relates to processes for preparing said crystalline materials and to methods of using said crystalline materials to treat a disease condition in which tyrosine kinase inhibition is beneficial.

SUMMARY

This invention is based, at least in part, on a co-crystal of Nilotinib hydrochloride and levulinic acid. Such a co-crystal provides a solid form of nilotinib hydrochloride that provides advantageous physical properties, particularly with respect to hygroscopicity.

In illustrative embodiments, there is provided a co-crystal of Nilotinib hydrochloride and levulinic acid wherein the molar ratio of Nilotinib hydrochloride to levulinic acid is approximately 1:2.

In illustrative embodiments, there is provided a co-crystal described herein characterized by a powder x-ray diffraction (PXRD) diffractogram comprising a peak, expressed in degrees two-theta, at 9.5+/−0.2.

In illustrative embodiments, there is provided a co-crystal described herein further characterized by at least four peaks, expressed in degrees two-theta, selected from the group consisting of: 9.0+/−0.2, 10.4+/−0.2, 16.3+/−0.2, 18.2+/−0.2, 19.1+/−0.2, 21.8+/−0.2, 22.5+/−0.2, 22.7+/−0.2, 25.8+/−0.2 and 27.5+/−0.2.

In illustrative embodiments, there is provided a co-crystal described herein characterized by a PXRD diffractogram substantially similar to the PXRD diffractogram depicted in FIG. 1.

In illustrative embodiments, there is provided a co-crystal described herein characterized by a DSC thermogram comprising an endothermic peak with a peak onset of approximately 144° C. and a peak maximum of about 146° C.

In illustrative embodiments, there is provided a process for the preparation of form APO-VII Nilotinib hydrochloride, the process comprising: a) obtaining a solution comprising Nilotinib free base and levulinic acid; b) treating the solution with hydrogen chloride thereby forming a mixture; and c) isolating form APO-VII Nilotinib hydrochloride from the mixture.

In illustrative embodiments, there is provided a process described herein wherein the solution comprising Nilotinib free base and levulinic acid comprises an amount of levulinic acid with respect to Nilotinib free base of from about 3 volumes to about 6 volumes.

In illustrative embodiments, there is provided a process described herein wherein the solution comprising Nilotinib free base and levulinic acid comprises an amount of levulinic acid with respect to Nilotinib free base of about 4 volumes.

In illustrative embodiments, there is provided a process described herein wherein the obtaining the solution comprises combining Nilotinib free base and levulinic acid thereby forming a combination and heating the combination to a temperature of between about 40° C. and about 90° C.

In illustrative embodiments, there is provided a process described herein wherein obtaining the solution comprises combining the Nilotinib free base and levulinic acid in the presence of an organic solvent selected from the group consisting of: alkyl esters, alkyl ethers, ketones and mixtures thereof.

In illustrative embodiments, there is provided a process described herein wherein the Nilotinib free base is combined with the organic solvent prior to combining with the levulinic acid.

In illustrative embodiments, there is provided a process described herein wherein the levulinic acid is combined with the organic solvent prior to combining with the Nilotinib free base.

In illustrative embodiments, there is provided a process described herein wherein the combination is combined with the organic solvent.

In illustrative embodiments, there is provided a process described herein wherein the organic solvent is selected from the group consisting of: methyl t-butyl ether, tetrahydrofuran, ethyl acetate, isopropyl acetate, and mixtures thereof.

In illustrative embodiments, there is provided a process described herein wherein the organic solvent is ethyl acetate.

In illustrative embodiments, there is provided a process described herein wherein the treating the solution with hydrogen chloride comprises treating the solution with a solution of hydrogen chloride in isopropanol.

In illustrative embodiments, there is provided a process described herein wherein the mixture is combined with an organic solvent prior to isolating the form APO-VII Nilotinib hydrochloride.

In illustrative embodiments, there is provided a process described herein wherein the organic solvent combined with the mixture is selected from the group consisting of: methyl t-butyl ether, tetrahydrofuran, ethyl acetate, isopropyl acetate, and mixtures thereof.

In illustrative embodiments, there is provided a process described herein wherein the organic solvent combined with the mixture is ethyl acetate.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention.

DETAILED DESCRIPTION

Figure 1:
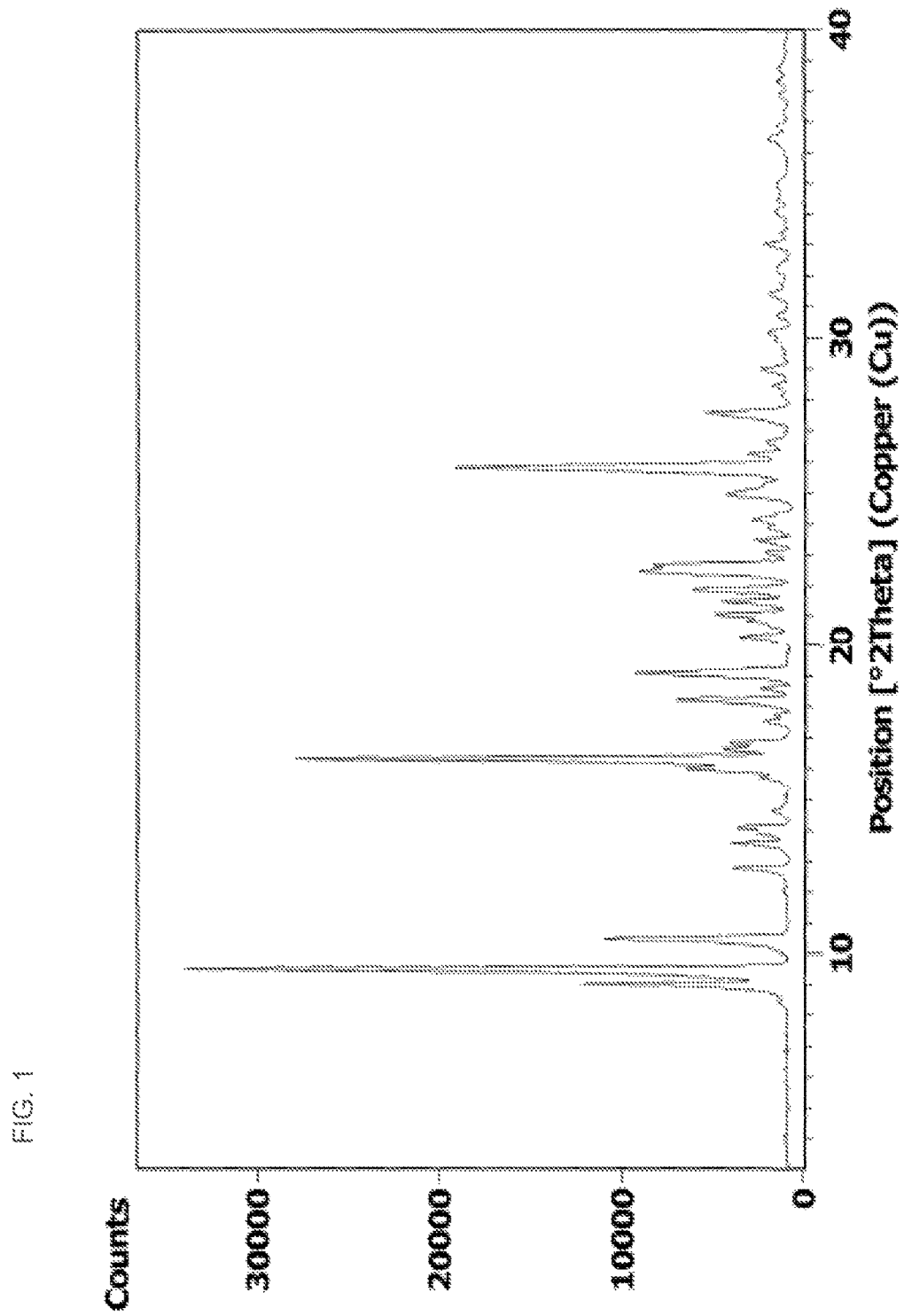
FIG. 1 is an experimental Powder X-Ray Diffraction (PXRD) diffractogram of form APO-VII of Nilotinib hydrochloride as prepared in Example 2.

When used in reference to a diffractogram, a spectrum and/or data presented in a graph, the term "substantially similar" means that the subject diffractogram, spectrum and/or data presented in a graph encompasses all diffractograms, spectra and/or data presented in graphs that vary within acceptable boundaries of experimentation that are known to a person of skill in the art. Such boundaries of experimentation will vary depending on the type of the subject diffractogram, spectrum and/or data presented in a graph, but will nevertheless be known to a person of skill in the art.

When used in reference to a peak in a powder X-ray diffraction (PXRD) diffractogram, the term "approximately" and/or "about" means that the peak may vary by ±0.2 degrees 2-theta of the subject value.

When used in reference to a peak in a DSC thermogram, the term "approximately" and/or "about" means that the peak may vary by ±1° C. of the subject value.

As used herein, when referring to a diffractogram, spectrum and/or to data presented in a graph, the term "peak" refers to a feature that one skilled in the art would recognize as not attributable to background noise.

Depending on the nature of the methodology applied and the scale selected to display results obtained from an X-ray diffraction analysis, an intensity of a peak obtained may vary quite dramatically. For example, it is possible to obtain a relative peak intensity of 1% when analyzing one sample of a substance, but another sample of the same substance may show a much different relative intensity for a peak at the same position. This may be due, in part, to the preferred orientation of the sample and its deviation from the ideal random sample orientation, sample preparation and the methodology applied. Such variations are known and understood by a person of skill in the art.

As used herein, the term "co-crystal" refers to a mixed crystal which contains two different components.

As used herein, the term "volumes" refers to the parts of solvent or liquids by volume (mL) with respect to the weight of solute (g). For example, when an experiment is conducted using 1 g of starting material and 100 mL of solvent, it is said that 100 volumes of solvent are used. For the purposes of the present invention, levulinic acid was used as a liquid.

Multi-component solid forms comprising more than one type of molecule, such as co-crystals may have some variability in the exact molar ratio of their components depending on a variety of conditions understood to a person of skill in the art. For example, a molar ratio of components within a co-crystal provides a person of skill in the art information as to the general relative quantities of the components of the co-crystal and, in many cases, the molar ratio may vary by plus or minus 20% from a stated range. For example, a molar ratio of 1:1 is understood to include the ratio 1:0.8 as well as 1:1.2 as well as all of the individual ratios in between.

The present invention provides a solid form of Nilotinib hydrochloride, termed herein APO-VII, which exists as a co-crystal with levulinic acid wherein the molar ratio of Nilotinib hydrochloride to levulinic acid is 1:2, respectively.

In an embodiment, the present invention provides form APO-VII of Nilotinib hydrochloride which may be characterized by a powder x-ray diffraction (PXRD) diffractogram comprising a peak, expressed in degrees two-theta, at 9.5+/−0.2.

In an embodiment, the present invention provides form APO-VII of Nilotinib hydrochloride which may be characterized by a powder x-ray diffraction (PXRD) diffractogram comprising a peak, expressed in degrees two-theta, at approximately 9.5, and further comprising at least four peaks, expressed in degrees two-theta, selected from the group consisting of: 9.0+/−0.2, 10.4+/−0.2, 16.3+/−0.2, 18.2+/−0.2, 19.1+/−0.2, 21.8+/−0.2, 22.5+/−0.2, 22.7+/−0.2, 25.8+/−0.2 and 27.5+/−0.2.

An illustrative PXRD diffractogram of form APO-VII is shown in FIG. 1.

Form APO-VII may have a reflection ("peak") at any one or more of the values expressed in degrees 2-theta given in Table 1. Although values are given in the tables below, APO-VII may be defined by the claimed peaks and a particular claim may be limited to one peak only, or several peaks. The form APO-VII does not have to include all or even many of the peaks listed in Table 1. Some illustrative and non-limiting possible observations regarding relative intensities of the peaks are set out in Table 1.

TABLE 1

Relative peak intensities of form APO-VII

| Angle 2-theta | Relative intensity % |
|---|---|
| 9.00 | 20.53 |
| 9.47 | 100.00 |
| 10.44 | 36.29 |
| 13.58 | 11.33 |
| 14.10 | 10.06 |
| 16.02 | 21.25 |
| 16.31 | 88.81 |

TABLE 1-continued

Relative peak intensities of form APO-VII

| Angle 2-theta | Relative intensity % |
|---|---|
| 16.64 | 12.82 |
| 16.84 | 11.87 |
| 18.21 | 23.73 |
| 19.08 | 29.56 |
| 20.30 | 12.01 |
| 21.04 | 16.01 |
| 21.45 | 13.66 |
| 21.85 | 19.37 |
| 22.46 | 28.36 |
| 22.67 | 22.27 |
| 24.93 | 10.32 |
| 25.79 | 60.96 |
| 26.22 | 10.82 |
| 27.51 | 15.84 |

In an embodiment, form APO-VII may be characterized by single crystal X-ray parameters approximately equal to those shown in Table 2.

TABLE 2

Single Crystal X-Ray Parameters of form APO-VII

| | | |
|---|---|---|
| Unit cell dimensions | a = 11.1569(7) Å | α = 99.934(3)° |
| | b = 11.4138(7) Å | β = 91.704(3)° |
| | c = 17.2029(10) Å | γ = 110.137(3)° |
| Crystal system | triclinic | |
| Space group | P-1 | |
| Volume | 2016.5(2) Å$^3$ | |
| Z | 2 | |
| Density (calculated) | 1.315 g/cm$^3$ | |

Figure 3:
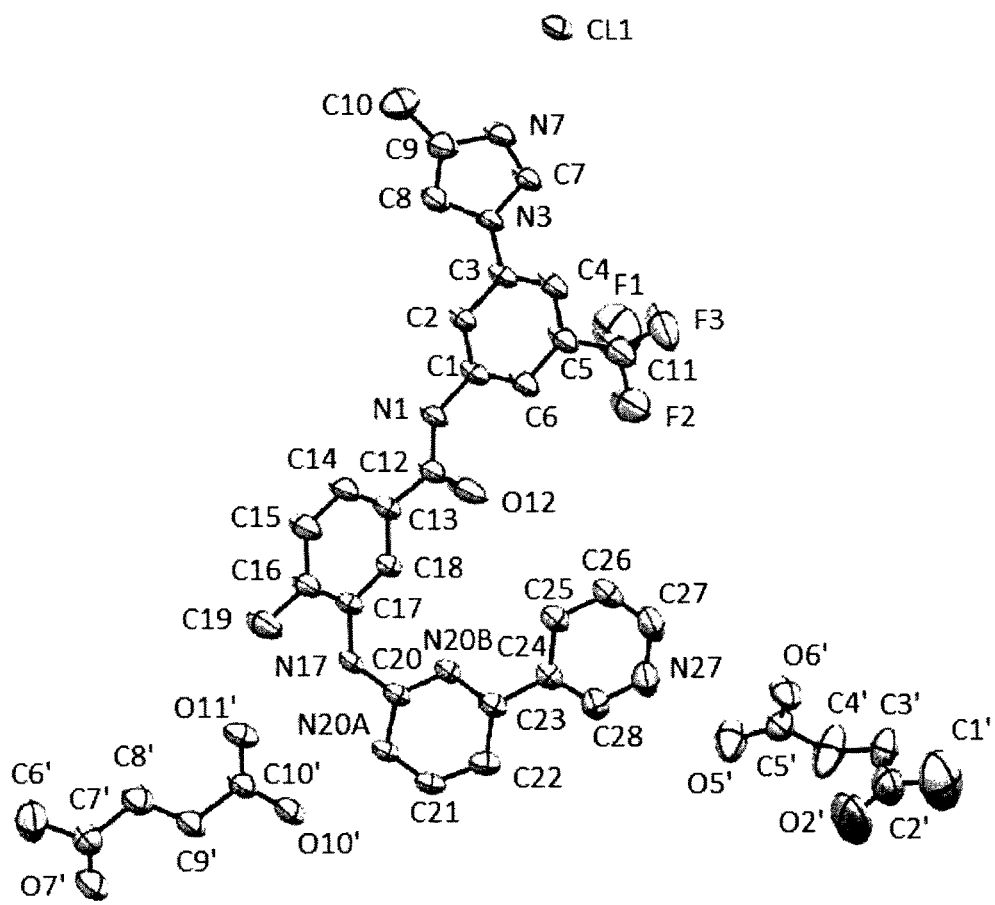
FIG. 3 is an Oak Ridge Thermal Ellipsoid Plot (ORTEP) Illustration of the single crystal x-ray of form APO-VII of Nilotinib hydrochloride prepared in Example 1.

An illustrative ORTEP illustration of form APO-VII based on the single crystal X-ray diffraction analysis is shown in FIG. 3. In this illustration, the crystal appears as a co-crystal of Nilotinib hydrochloride and two neutral molecules of levulinic acid.

Figure 2:
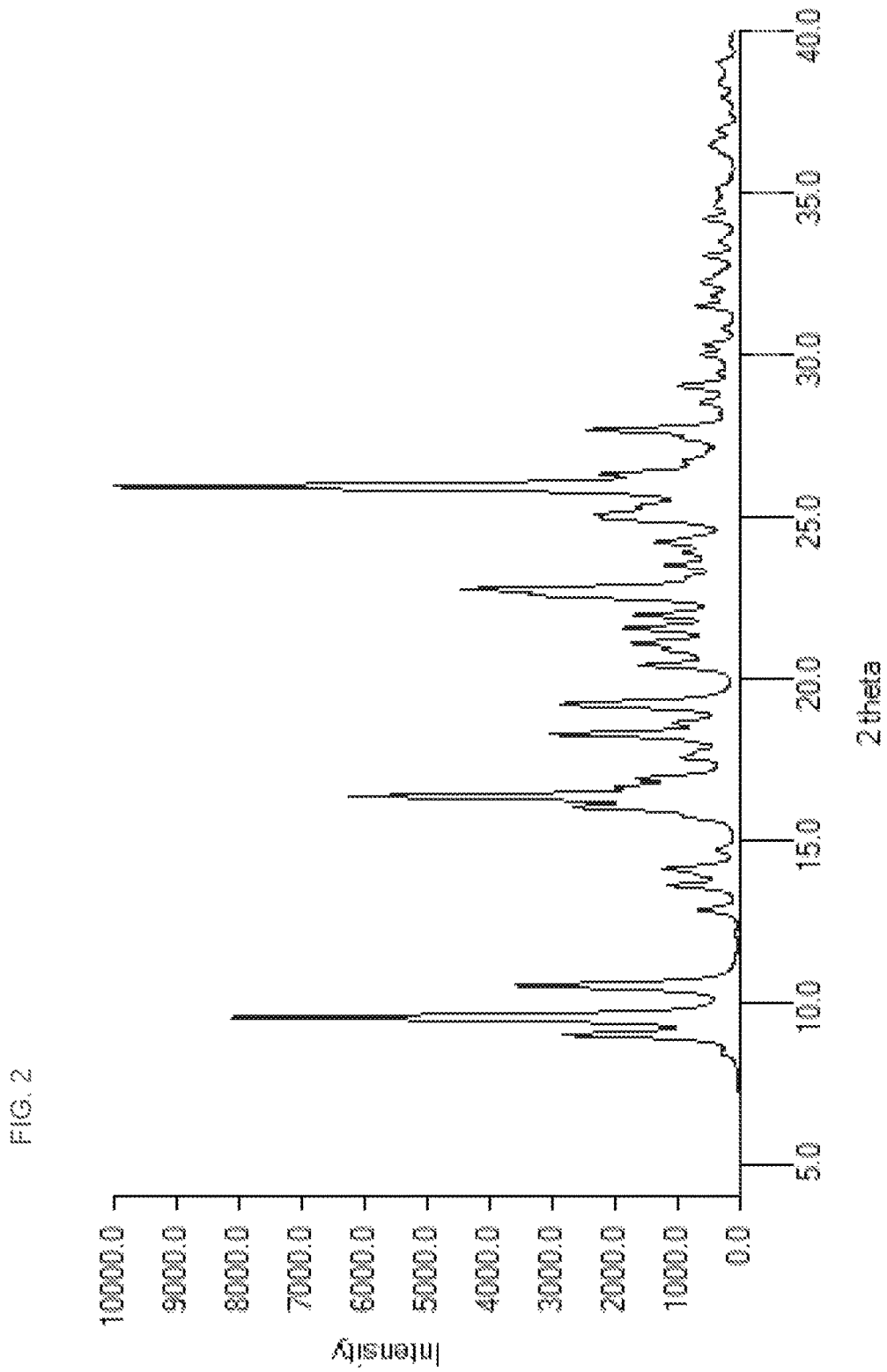
FIG. 2 is a calculated Powder X-Ray Diffraction (PXRD) diffractogram of form APO-VII of Nilotinib hydrochloride based on the single crystal x-ray analysis of the sample prepared in Example 1.

A calculated PXRD diffractogram based on the single crystal x-ray analysis is shown in FIG. 2.

Figure 4:
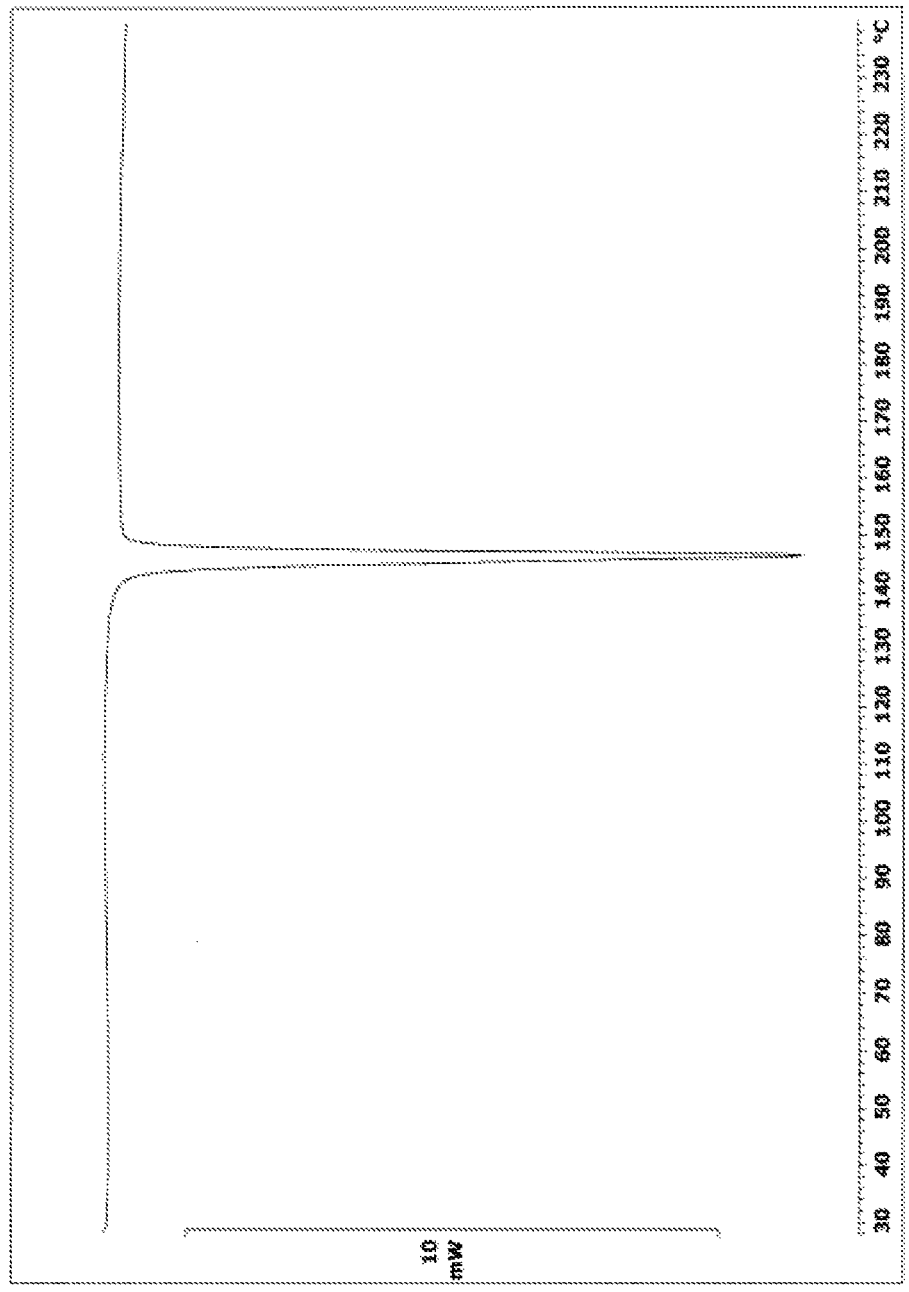
FIG. 4 is a Differential Scanning calorimetry (DSC) thermogram of form APO-VII of Nilotinib hydrochloride as prepared in Example 2.

An illustrative DSC thermogram of form APO-VII is shown in FIG. 4. The DSC thermogram shown in FIG. 4 may be illustrative of the type of results obtained when analysing form APO-VII by DSC. The DSC thermogram may be further characterized by a peak endotherm with an onset temperature of approximately 144° C. and a peak maximum of approximately 146° C.

Form APO-VII Nilotinib hydrochloride may be prepared by a process comprising:
  a) obtaining a solution comprising Nilotinib free base and levulinic acid;
  b) treating the solution with hydrogen chloride thereby forming a mixture; and
  c) isolating form APO-VII Nilotinib hydrochloride from the mixture.

One method for obtaining the solution comprising Nilotinib freebase and levulinic acid includes dissolving Nilotinib free base in levulinic acid. Often about 3 volumes to about 6 volumes of levulinic acid with respect to the weight of Nilotinib free base may be used to prepare the solution. It is preferable that enough levulinic acid is used to provide suitable stirrability prior to dissolution. In this regard, often an amount of levulinic acid used to prepare the solution is about four volumes with respect to the weight of Nilotinib free base and this amount provides a desirable stirrability. Often, dissolution is achieved at elevated temperatures between about 40° C. to about 90° C. Preferably, the time between obtaining a solution and treating the solution with hydrogen chloride is minimized so as to avoid precipitation of a solid from the solution. In particular, the time between obtaining a solution and treating the solution with hydrogen chloride should not exceed the time it takes to observe precipitation of a solid from the solution. The amount of time it takes to observe precipitation is dependent on the nature of the solution, including temperature and ratio of components in the solution.

In some embodiments, the hydrogen chloride used to treat the solution comprising Nilotinib free base and levulinic acid may be provided as a second solution in an organic solvent such as isopropanol. In some embodiments, an aqueous solution of hydrogen chloride may be used. It is preferable to minimize the amount of water used. In some embodiments, the hydrogen chloride may be provided as a gas. The treating of the solution with hydrogen chloride may occur at a temperature of between about 20° C. to about 60° C.

In some embodiments, the solution or the mixture may contain a further organic solvent. The organic solvent may be selected from the group consisting of alkyl ethers (for example, methyl t-butyl ether, tetrahydrofuran), alkyl esters (for example, ethyl acetate, isopropyl acetate), ketones (for example, acetone) and mixtures thereof. Often, the organic solvent is ethyl acetate. Often, about 2 volumes to about 8 volumes of organic solvent with respect to the weight of Nilotinib free base may be used.

The mixture may be stirred for a suitable amount of time to allow the formation of APO-VII. Often, the mixture is stirred for about 18 hours at about 20° C. to about 40° C. before isolating form APO-VII.

Once isolated, the Form APO-VII may be washed with a suitable volatile organic solvent such as ethyl acetate.

Following isolation, form APO-VII may be dried in vacuo at a temperature of from about 20° C. to about 80° C. The drying time may vary depending on the conditions, with a minimum of about 16 hours often employed.

EXAMPLES

The following examples are illustrative of some of the embodiments of the invention described herein. These examples do not limit the spirit or scope of the invention in any way.

Single Crystal X-Ray Diffraction Analysis:

The form APO-VII prepared in Example 1 was used for single crystal x-ray analysis. Data were collected on a Bruker Smart Apex2 Mo diffractometer with a Triumph monochromator. A total of 2020 frames were collected in 5 ω-scans. The total exposure time was 16.83 hours. The frames were integrated with the Bruker SAINT software package using a narrow-frame algorithm. The integration of the data using a triclinic unit cell yielded a total of 34979 reflections to a maximum θ angle of 25.54° (0.82 Å resolution), of which 7472 were independent (average redundancy 4.681, completeness=99.0%, $R_{int}$=4.68%, $R_{sig}$=4.13%) and 4725 (63.24%) were greater than 2σ($F^2$). The final cell constants of a=11.1569(7) Å, b=11.4138(7) Å, c=17.2029(10) Å, α=99.934(3)°, β=91.704(3)°, γ=110.137(3)°, volume=2016.5(2) Å$^3$, are based upon the refinement of the XYZ-centroids of 5639 reflections above 20 σ(I) with 4.787°<2θ<43.75°. Data were corrected for absorption effects using the numerical method (SADABS). The ratio of minimum to maximum apparent transmission was 0.847. The calculated minimum and maximum transmission coefficients (based on crystal size) are 0.9480 and 0.9810. Non-hydrogen atoms were found by direct methods. All hydrogen atoms were located in the difference map. The final anisotropic full-matrix least-squares refinement on $F^2$ with 677 variables converged at R1=5.06%, for the observed data and wR2=15.68% for all data. The goodness-of-fit was 1.031. The largest peak in the final difference electron density synthesis was 0.308 e$^-$/Å$^3$ and the largest hole was −0.282 e$^-$/Å$^3$ with an RMS deviation of 0.047 e$^-$/Å$^3$. On the basis of the final model, the calculated density was 1.315 g/cm$^3$ and F(000), 832 e$^-$. Crystallographic data for the sample of form APO-VII prepared in Example 1 is shown in Table 3.

TABLE 3

Sample and crystal data for Form APO-VII

| | |
|---|---|
| Moiety formula | $C_{28}H_{23}F_3N_7O^+$, $Cl^-$, $2(C_5H_8O_3)$ |
| Formula weight | 798.21 g/mol |
| Temperature | 296(2) K |
| Wavelength | 0.71073 Å |
| Crystal size | 0.120 × 0.175 × 0.328 mm |
| Crystal habit | clear pale yellow fragment |
| Crystal system | triclinic |
| Space group | P-1 |
| Unit cell dimensions | a = 11.1569(7) Å   α = 99.934(3)° |
| | b = 11.4138(7) Å   β = 91.704(3)° |
| | c = 17.2029(10) Å   γ = 110.137(3)° |
| Volume | 2016.5(2) Å$^3$ |
| Z | 2 |
| Density (calculated) | 1.315 g/cm$^3$ |
| Absorption coefficient | 0.164 mm$^{-1}$ |
| F(000) | 832 |

Powder X-Ray Diffraction Analysis:

Data were acquired on a PANanalytical X-Pert Pro MPD diffractometer with fixed divergence slits and an X'Celerator RIMS detector. The diffractometer was configured in Bragg-Brentano geometry; data was collected over a 2-theta range of 3 to 40 degrees using CuKa radiation at a power of 40 mA and 45 kV. CuKβ radiation was removed using a divergent beam nickel filter. A step size of 0.017 degrees was used. Samples were rotated to reduce preferred orientation effects. Samples were lightly ground prior to analysis.

Calculated Powder X-Ray Diffraction Diffractograms

Powder diffractograms were calculated from single crystal X-ray data using the SHELXTL package of programs, including XFOG (SHELXTL, Bruker AXS, XFOG, Version 5.1 00, 1997) and XPOW (SHELXTL, Bruker AXS, XPOW, Version 5.102, 1997-2000). The appropriate wavelength needed for overlay graphics was added using the XCH file exchange program (SHELXTL, Bruker AXS, XCH, Version 5.0.4, 1995-2001).

Differential Scanning Calorimetry Analysis:

The DSC thermograms were collected on a Mettler-Toledo 821e instrument. Samples (1-5 mg) were weighed into a 40 μL aluminum pan and were crimped closed with an aluminum lid. The samples were analyzed under a flow of nitrogen (ca. 50 mL/min) at a scan rate of 10° C./minute.

The assay of the levulinic acid used herein was about 98 wt %.

Example 1

Preparation of Single Crystals X-Ray Analysis

A suspension of form APO-VII (0.7 g, prepared by the method described in Example 2) and levulinic acid (10.2 g) was warmed to 60° C. to achieve dissolution of APO-VII.

The solution was then transferred into 4 separate vials and held at 54° C. The temperature of the solutions was slowly reduced at a rate of 420 C. per day until a final temperature of 25° C. was reached. FIG. 3 depicts an ORTEP illustration of the single crystal x-ray of form APO-VII of Nilotinib hydrochloride prepared by this method. FIG. 2 depicts a calculated PXRD based on the single crystal analysis of this sample.

Example 2

Preparation of Form APO-VII Nilotinib Hydrochloride

A suspension of Nilotinib free base (50 g) and levulinic acid (283.3 g) was warmed to 80° C. to 85° C. and maintained until complete dissolution was observed. Once complete dissolution was observed, the yellow to amber solution was cooled to 40° C. to 45° C. followed immediately by the addition of a solution of hydrogen chloride in isopropanol (20.37% w/w, 1.0 eq). The solution was allowed to stir for 1 hour at 40° C. to 45° C. A solid started to precipitate slowly after the addition of the hydrogen chloride solution. After stirring for 1 hour, ethyl acetate (451.3 g) was added to the suspension over about 30 minutes. The suspension was then cooled to 20° C. to 25° C. and allowed to stir for about 23 hours. The suspension was filtered, rinsed with ethyl acetate (2×200 mL), and dried in vacuo (40 torr) at about 45° C. for about 17 hours. Form APO-VII was obtained as a pale yellow to off-white solid (74.4 g, 98.7% yield). FIG. 1 depicts a PXRD diffractogram that was obtained using sample prepared by this method.

Example 3

Preparation of Form APO-VII Nilotinib Hydrochloride

A suspension of Nilotinib free base (10 g) and levulinic acid (56.7 g) was warmed to 80° C. to 85° C. and maintained until complete dissolution was observed. Once complete dissolution was observed, the yellow to amber solution was cooled to 40° C. to 45° C. followed immediately by the addition of a solution of hydrogen chloride in isopropanol (20.37% w/w, 1.0 eq). The solution was allowed to stir for 30 minutes at 40° C. to 45° C. A solid started to precipitate slowly after the addition of the hydrogen chloride solution. The suspension was then cooled to 20° C. to 25° C. and allowed to stir for about 24 hours. The suspension was filtered, rinsed with ethyl acetate (2×40 mL) and dried in vacuo (40 torr) at about 45° C. for about 23 hours. Form APO-VII was obtained as a pale yellow to off-white solid (14.4 g, 95.6% yield).

Example 4

Preparation of Form APO-VII Nilotinib Hydrochloride

A suspension of Nilotinib free base (3 g) and levulinic acid (13.6 g) was warmed to 80° C. to 85° C. and maintained until complete dissolution was observed. Once complete dissolution was observed, the yellow to amber solution was cooled to 40° C. to 45° C. followed immediately by the addition of a solution of hydrogen chloride in isopropanol (20.37% w/w, 1.0 eq). The solution was allowed to stir for 3 hours at 40° C. to 45° C. A solid started to precipitate slowly after the addition of the hydrogen chloride solution. After stirring for 3 hours, ethyl acetate (16.2 g) was added to the suspension over about 15 minutes. The suspension was then cooled to 20° C. to 25° C. and allowed to stir for about 24 hours. The suspension was filtered, rinsed with ethyl acetate (2×12 mL) and dried in vacuo (40 torr) at about 40° C. for about 18 hours. Form APO-VII was obtained as a pale yellow to off-white solid (4.3 g, 95.1% yield).

Example 5

Preparation of Form APO-VII Nilotinib Hydrochloride

A suspension of Nilotinib free base (10 g) and levulinic acid (56.7 g) was warmed to 80° C. to 85° C. and maintained until complete dissolution was observed. Once complete dissolution was observed, the yellow to amber solution was cooled to 40° C. to 45° C. followed immediately by the addition of a solution of hydrogen chloride in isopropanol (20.37% w/w, 1.0 eq). The solution was allowed to stir for 30 minutes at 40° C. to 45° C. A solid started to precipitate slowly after the addition of the hydrogen chloride solution. After stirring for 30 minutes, ethyl acetate (54.1 g) was added to the suspension over about 15 minutes. The suspension was then cooled to 20° C. to 25° C. and allowed to stir for about 23 hours. The suspension was filtered, rinsed with ethyl acetate (2×40 mL), and dried in vacuo (40 torr) at about 60° C. for about 17 hours. Form APO-VII was obtained as a pale yellow to off-white solid (14.6 g, 96.9% yield).

Example 6

Preparation of Form APO-VII Nilotinib Hydrochloride

A suspension of Nilotinib free base (5 g) and levulinic acid (28.4 g) was warmed to 55° C. to 60° C. and maintained until complete dissolution was observed. Once complete dissolution was observed, a solution of hydrogen chloride in isopropanol (23.1% w/w, 1.0 eq) was added. The solution was allowed to stir for 30 minutes at 55° C. to 60° C. A solid started to precipitate slowly after the addition of the hydrogen chloride solution. After stirring for 30 minutes, isopropyl acetate (13.1 g) was added to the suspension over about 5 minutes. The suspension was then cooled to 20° C. to 25° C. and allowed to stir for about 24 hours. The suspension was filtered, rinsed with isopropyl acetate (2×20 mL), and dried in vacuo (40 torr) at about 60° C. for about 72 hours. Form APO-VII was obtained as a pale yellow to off-white solid (6.8 g, 90.2% yield).

Example 7

Preparation of Form APO-VII Nilotinib Hydrochloride

A suspension of Nilotinib free base (5 g) and levulinic acid (28.4 g) was warmed to 55° C. to 60° C. and maintained until complete dissolution was observed. Once complete dissolution was observed, a solution of hydrogen chloride in isopropanol (23.1% w/w, 1.0 eq) was added. The solution was allowed to stir for 30 minutes at 55° C. to 60° C. A solid started to precipitate slowly after the addition of the hydrogen chloride solution. After stirring for 30 minutes, methyl t-butyl ether (11.1 g) was added to the suspension over about 5 minutes. The suspension was then cooled to 20° C. to 25° C. and allowed to stir for about 24 hours. The suspension was filtered, rinsed with methyl t-butyl ether (2×20 mL), and dried in vacuo (40 torr) at about 60° C. for about 72 hours. Form APO-VII was obtained as a pale yellow to off-white solid (7.5 g, 99.5% yield).

Example 8

Preparation of Form APO-VII Nilotinib Hydrochloride

A suspension of Nilotinib free base (5 g) and levulinic acid (29.0 g) was warmed to 55° C. to 60° C. and maintained until complete dissolution was observed. Once complete dissolution was observed, a solution of hydrogen chloride in isopropanol (23.1% w/w, 1.0 eq) was added. The solution was allowed to stir for 30 minutes at 55° C. to 60° C. A solid started to precipitate slowly after the addition of the hydrogen chloride solution. After stirring for 30 minutes, acetone (11.9 g) was added to the suspension over about 5 minutes. The suspension was then cooled to 20° C. to 25° C. and allowed to stir for about 24 hours. The suspension was filtered, rinsed with acetone (2×20 mL), and dried in vacuo (40 torr) at about 60° C. for about 72 hours. Form APO-VII was obtained as a pale yellow to off-white solid (7.1 g, 94.2% yield).

Example 9

Preparation of Form APO-VII Nilotinib Hydrochloride

A suspension of Nilotinib free base (5 g) and levulinic acid (28.4 g) was warmed to 55° C. to 60° C. and maintained until complete dissolution was observed. Once complete dissolution was observed, a solution of hydrogen chloride in isopropanol (23.1% w/w, 1.0 eq) was added. The solution was allowed to stir for 30 minutes at 55° C. to 60° C. A solid started to precipitate slowly after the addition of the hydrogen chloride solution. After stirring for 30 minutes, tetrahydrofuran (13.3 g) was added to the suspension over about 5 minutes. The suspension was then cooled to 20° C. to 25° C. and allowed to stir for about 24 hours. The suspension was filtered, rinsed with tetrahydrofuran (2×20 mL), and dried in vacuo (40 torr) at about 60° C. for about 72 hours. Form APO-VII was obtained as a pale yellow to off-white solid (6.9 g, 91.7% yield).

Example 10

Comparative Hygroscopicity Testing of Form APO-VII Nilotinib Hydrochloride and Form APO-III Nilotinib Hydrochloride The hygroscopicity of form APO-III as reported in WO 2014/059518 A1 was compared with the hygroscopicity of the form APO-VII of the present invention. The results are shown in Table 4.

TABLE 4

Comparative Hygroscopicity Testing

| Sample | Water content of sample before testing (% w/w) | Water content of sample after testing (% w/w) | Increase in water content |
|---|---|---|---|
| Form APO-III | 0.2876 | 3.5671 | 3.2795 |
| Form APO-VII | 0.2945 | 0.4757 | 0.1812 |

The hygroscopicity testing was conducted by placing 1 g of each sample in an unstoppered weighing vessel in a desiccator containing a saturated ammonium sulphate solution. The desiccator was placed in an oven at 25° C. for 24 hours. The water content was measured before and after the testing by Karl Fischer (KF) analysis.

Example 11

Preparation of Nilotinib Free Base

Nilotinib free base for use in the experiments herein was prepared according to the following method. Nilotinib hydrochloride monohydrate (200.2 g) was suspended in N-methyl-2-pyrrolidone (515.2 g) at 20° C. to 25° C. The suspension was treated with sodium hydroxide (35.2 g) followed immediately by addition of water (1200 mL) at 20° C. to 25° C. The suspension was allowed to stir at 20° C. to 25° C. for about 3 hours. The solid was isolated and washed with water (4×400 mL) and isopropanol (1×500 mL). The solid was dried under vacuum at 60° C. for about 24 hours.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to the present invention. Any priority document(s) are incorporated herein by reference as if each individual priority document were specifically and individually indicated to be incorporated by reference herein and as though fully set forth herein. The invention includes all embodiments and variations substantially as hereinbefore described and with reference to the examples and drawings.

What is claimed is:

1. A co-crystal of Nilotinib hydrochloride and levulinic acid wherein the molar ratio of Nilotinib hydrochloride to levulinic acid is approximately 1:2.

2. The co-crystal of claim 1, characterized by a powder x-ray diffraction (PXRD) diffractogram comprising a peak, expressed in degrees two-theta, at 9.5+/−0.2.

3. The co-crystal of claim 2, further characterized by at least four peaks, expressed in degrees two-theta, selected from the group consisting of: 9.0+/−0.2, 10.4+/−0.2, 16.3+/−0.2, 18.2+/−0.2, 19.1+/−0.2, 21.8+/−0.2, 22.5+/−0.2, 22.7+/−0.2, 25.8+/−0.2 and 27.5+/−0.2.

4. The co-crystal of claim 1, characterized by a PXRD diffractogram substantially similar to the PXRD diffractogram depicted in FIG. 1.

5. The co-crystal of claim 1, characterized by a DSC thermogram comprising an endothermic peak with a peak onset of approximately 144° C. and a peak maximum of about 146° C.

6. A process for the preparation of form APO-VII Nilotinib hydrochloride, the process comprising:
   a) obtaining a solution comprising Nilotinib free base and levulinic acid;
   b) treating the solution with hydrogen chloride thereby forming a mixture; and
   c) isolating form APO-VII Nilotinib hydrochloride from the mixture.

7. The process of claim 6, wherein the solution comprising Nilotinib free base and levulinic acid comprises an amount of levulinic acid with respect to Nilotinib free base of from about 3 volumes to about 6 volumes.

8. The process of claim 7, wherein the solution comprising Nilotinib free base and levulinic acid comprises an amount of levulinic acid with respect to Nilotinib free base of about 4 volumes.

9. The process of claim 7, wherein obtaining the solution comprises combining Nilotinib free base and levulinic acid thereby forming a combination and heating the combination to a temperature of between about 40° C. and about 90° C.

10. The process of claim 6, wherein obtaining the solution comprises combining the Nilotinib free base and levulinic acid in the presence of an organic solvent selected from the group consisting of: alkyl esters, alkyl ethers, ketones and mixtures thereof.

11. The process of claim 10, wherein the organic solvent is selected from the group consisting of: methyl t-butyl ether, tetrahydrofuran, ethyl acetate, isopropyl acetate, and mixtures thereof.

12. The process of claim 11, wherein the organic solvent is ethyl acetate.

13. The process of claim 6, wherein the treating the solution with hydrogen chloride comprises treating the solution with an aqueous solution of hydrogen chloride.

14. The process of claim 13, wherein the mixture is combined with an organic solvent prior to isolating the form APO-VII Nilotinib hydrochloride.

15. The process of claim 14, wherein the organic solvent combined with the mixture is selected from the group consisting of: methyl t-butyl ether, tetrahydrofuran, ethyl acetate, isopropyl acetate, and mixtures thereof.

16. The process of claim 14, wherein the organic solvent combined with the mixture is ethyl acetate.

17. The process of claim 12, wherein the amount of ethyl acetate with respect to Nilotinib free base is from about 2 volumes to about 8 volumes.

18. The process of claim 17, wherein the amount of ethyl acetate with respect to Nilotinib free base is about 2 volumes.

19. The process of claim 6, wherein the treating the solution with hydrogen chloride comprises treating the solution at a temperature of between about 40° C. and about 50° C.

* * * * *